(12) United States Patent  (10) Patent No.: US 7,442,814 B2
Saleh et al.  (45) Date of Patent: Oct. 28, 2008

(54) 1-METHOXY-2-PHENYL ETHENES USEFUL FOR THE PREPARATION OF 5-CARBOXALDEHYDE-2-3-DIHYDROBENZOXEPINES

(75) Inventors: Twana Saleh, Chennevieres sur Marne (FR); Bernard Boudet, Pithiviers (FR)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/587,488

(22) PCT Filed: Apr. 5, 2005

(86) PCT No.: PCT/EP2005/003550

§ 371 (c)(1),
(2), (4) Date: Oct. 26, 2006

(87) PCT Pub. No.: WO2005/102977

PCT Pub. Date: Nov. 3, 2005

(65) Prior Publication Data

US 2007/0219381 A1  Sep. 20, 2007

(30) Foreign Application Priority Data

Apr. 27, 2004 (EP) ................... 04291091

(51) Int. Cl.
*C07D 303/00* (2006.01)
*A01N 57/00* (2006.01)
(52) U.S. Cl. ........................ 549/453; 514/92
(58) Field of Classification Search .......... 549/430, 549/453
See application file for complete search history.

(56) References Cited

U.S. PATENT DOCUMENTS 6,596,758 B1  7/2003  Brunet et al.

FOREIGN PATENT DOCUMENTS

WO  WO 00/39113 A  7/2000

OTHER PUBLICATIONS

Paquette et al Journal of the American Chemical Society 1983, 105, 7352-7358.*
F. Zaragoza Dorwald "Side Reactions in Organic Synthesis: A Guide to Successful Synthesis Design" 2005, Wiley-VCH Verlag GmbH & Co. KGaA, Wienheim.*
March, J. Advanced Organic Chemistry: Reactions, Mechanisms and Structure, 5th Ed. John Wiley & Sons, Inc. 2001, pp. 282-284.*
Margarie et al., Synthesis of (+/−)—Vitrenal, chemistry letters, 1982, pp. 1143-1146, p. 1144.
Paquette L A et al., Tri luinane Sesqui Terpenes An Iterative Highly Stereo Controlled Synthesis of Racemic Silphinene, Journal of the American Chemical Society, vol. 105, No. 25, 1983, pp. 7352-7358.
Database Caplus Online 1995, XP002300264, Retrieved from STN Database Accession No. 1995: 6597611 Caplus cited in the application DN: 123:285684.

* cited by examiner

*Primary Examiner*—Rita Desai
*Assistant Examiner*—John Mabry
(74) *Attorney, Agent, or Firm*—Miller, White, Zelano, Branigan, P.C.

(57) ABSTRACT

The present invention relates to the compounds of general formula (I)

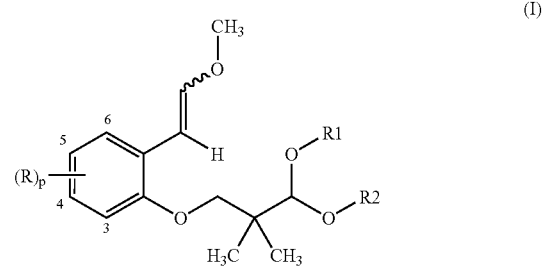

wherein R, $R_1$, $R_2$ are as defined in claim 1.

Compounds of formula (I) are particularly useful for preparing 3,3-dimethyl-5-formyl-2,3-dihydrobenzoxepines derivatives.

26 Claims, No Drawings

1-METHOXY-2-PHENYL ETHENES USEFUL FOR THE PREPARATION OF 5-CARBOXALDEHYDE-2-3-DIHYDROBENZOXEPINES

FIELD OF THE INVENTION

The present invention relates to 1-methoxy-2-phenyl-ethene derivatives and their use for the preparation of 3,3-dimethyl-5-formyl-2,3-dihydro-benzoxepines derivatives.

BACKGROUND OF THE INVENTION 3,3-dimethyl-5-formyl-2,3-dihydrobenzoxepine derivatives (formula II):

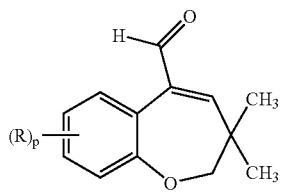

(II)

are disclosed in EP 1140893 B1 and U.S. Pat. No. 6,596,758 patents as intermediates for the preparation of 5-(3,3-dim-ethyl-2,3-dihydro benzoxepin-5-yl)-2,4-pentadienoic acid derivatives useful for treating dyslipidemias, athero-sclerosis and diabetes.

In these patents, compounds of formula II are prepared according to the following scheme:

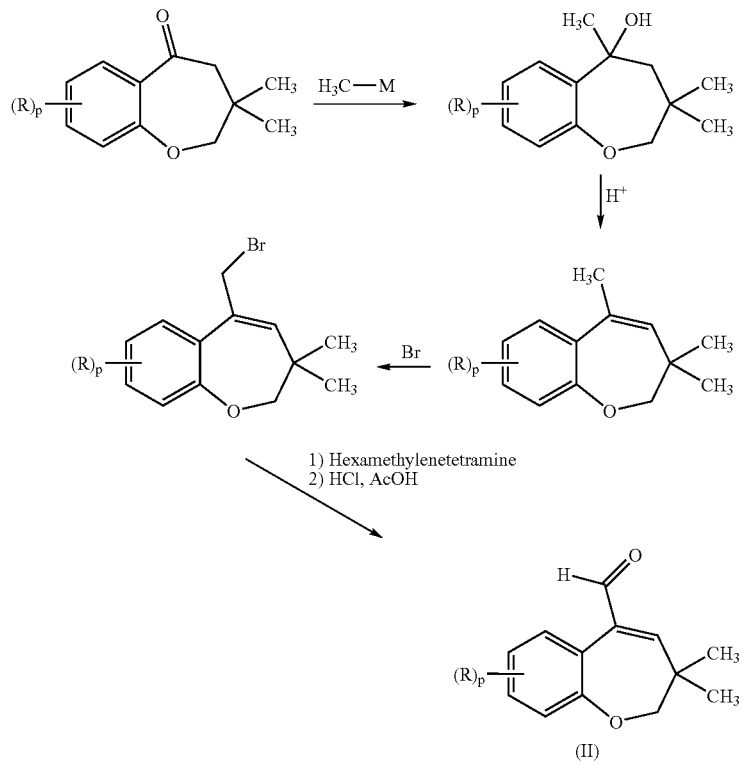

Scheme 1: a benzoxepinone is reacted with an organomettallic compound CH$_3$-M in which M is -Mg-hal (where hal is a halogen atom) or else M is Li.

This synthetic method involves four chemical steps starting from benzoxepinone and the yields, as reported, are moderate.

Furthermore, this synthetic pathway cannot be easily scaled up to commercial implementation.

It now has been found a novel improved synthetic route for preparing the compounds of formula (II) which is unexpectedly applicable at industrial scale.

Advantageously, the compounds of formula (II) can be obtained in only three steps, each being characterized by high yields.

As another advantage, the invention provides an economical and efficient route for preparing the compounds of formula (II).

According to the present invention, compounds of formula (II) are prepared from new compounds of formula (I):

Thus, in one aspect, the present invention is related to compounds of general formula (I):

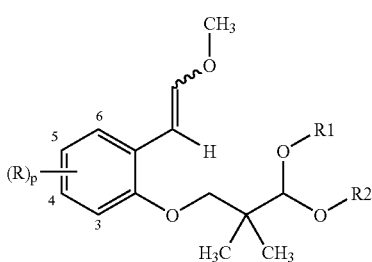

(I)

Each of R is independently chosen from a halogen atom; a cyano group; a nitro group; a carboxy group; an optionally halogenated ($C_1$-$C_{18}$)alkoxycarbonyl group; an $R_a$—CO—NH— or $R_aR_bN$—CO— group [in which $R_a$ and $R_b$ independently represent optionally halogenated ($C_1$-$C_{18}$)alkyl; a hydrogen atom; ($C_6$-$C_{10}$)aryl or ($C_6$-$C_{10}$)aryl($C_1$-$C_5$)alkyl (where the aryl parts are optionally substituted by a halogen atom, by an optionally halogenated ($C_1$-$C_5$)alkyl group or by an optionally halogenated ($C_1$-$C_5$)alkoxy group); ($C_3$-$C_{12}$) cycloalkyl optionally substituted by a halogen atom, by an optionally halogenated ($C_1$-$C_5$)alkyl group or by an optionally halogenated ($C_1$-$C_5$)alkoxy group]; an optionally halogenated ($C_1$-$C_{18}$)alkyl group; optionally halogenated ($C_1$-$C_{18}$)alkoxy; and ($C_6$-$C_{10}$)aryl, ($C_6$-$C_{10}$)aryl($C_1$-$C_5$)alkyl, ($C_6$-$C_{10}$)aryloxy, ($C_3$-$C_{12}$)cyclo-alkyl, ($C_3$-$C_{12}$)cycloalkenyl, ($C_3$-$C_{12}$)cycloalkyloxy, ($C_3$-$C_{12}$)cycloalkenyloxy; ($C_6$-$C_{10}$)aryloxycarbonyl or ($C_6$-$C_{10}$)arylcarbonyl; in which the aryl, cycloalkyl and cycloalkenyl parts are optionally substituted by a halogen atom, by an optionally halogenated ($C_1$-$C_5$)alkyl or by an optionally halogenated ($C_1$-$C_5$)alkoxy;

p represents 0, 1, 2, 3 or 4;

$R_1$ and $R_2$ are a ($C_1$-$C_{18}$)alkyl group or form together —$(CH_2)_n$— wherein n represents 2, 3 or 4.

The formula (I) encompasses all types of geometric isomers and stereoisomers of the compounds of formula (I).

As used above and throughout the description of the invention, the following terms, unless otherwise indicated, shall be understood to have the following meanings.

"Alkyl" means an aliphatic hydrocarbon group which may be straight or branched, having 1 to 18 carbon atoms in the chain. Preferred alkyl groups have 1 to 12 carbon atoms in the chain.

"Branched alkyl" means that one or more lower alkyl groups such as methyl, ethyl or propyl are attached to a linear alkyl chain.

"Lower alkyl" means an alkyl group with 1 to about 4 carbon atoms in the chain which may be straight or branched.

Exemplary alkyl groups include methyl, ethyl, propyl, isopropyl, butyl, tert-butyl, isobutyl, pentyl, hexyl, heptyl, octyl, nonyl, decyl, undecyl, dodecyl, tridecyl, tetradecyl, pentadecyl, hexadecyl, heptadecyl or octadecyl.

The alkyl group may be substituted by one or more halogen atoms representing thus an "halogenoalkyl" group.

"Halogen atoms" means fluorine, chlorine, bromine or iodine atoms. Preferred are fluorine, chlorine or bromine atoms and more preferred is fluorine atoms.

The "halogenoalkyl" groups may thus refer to "perfluoroalkyl", which means groups corresponding to the formula "—$C_nF_{2n+1}$" wherein n represents 1 to 18.

Examples of perfluoroalkyl groups are pentafluoroethyl or trifluoro-methyl.

"Alkoxy" means an alkyl-O— group wherein the alkyl group is as herein described. Exemplary alkoxy groups include methoxy, ethoxy, isopropyloxy, butoxy and hexyloxy radicals.

"Cycloalkyl" means a non-aromatic mono- or multicyclic ring system of about 3 to 12 carbon atoms. Preferred ring sizes of the ring system include about 3 to 8 and more preferably 5 to 6 ring atoms. The cycloalkyl is optionally substituted with one or more "ring system substituents" which may be the same or different, and are as defined herein. Exemplary monocyclic cycloalkyl include cyclopropyl, cyclobutyl, cyclopentyl, cyclohexyl, cycloheptyl, cyclooctyl, cyclononyl, cyclodecyl, cycloundecyl, cyclododecyl and the like.

Exemplary multicyclic cycloalkyl include 1-decalyn, norbornyl and the like.

"Cycloalkenyl" means a non-aromatic mono- or multicyclic ring system of about 3 to about 12 carbon atoms, preferably of about 5 to about 10 carbon atoms, and which contain at least one carbon-carbon double bond.

Preferred ring size of rings of the ring system include about 5 to about 6 ring atoms. The cycloalkenyl is optionally substituted with one or more "ring system substituents" which may be the same or different, and are as defined herein. Exemplary monocyclic cycloalkenyl include cyclopentenyl, cyclohexenyl, cycloheptenyl and the like. An exemplary multicyclic cycloalkenyl is norbornylenyl.

"Aryl" means an aromatic monocyclic or multicyclic ring system of about 6 to about 10 carbon atoms. The aryl is optionally substituted with one or more "ring system substituents" which may be the same or different and are as defined herein. Exemplary aryl groups include phenyl or naphtyl, or substituted phenyl or substituted naphtyl.

"Alkenyl" means an aliphatic hydrocarbon group containing one or more carbon-carbon double bond and which may be straight or branched, having about 2 to about 12 carbon atoms in the chain, and more preferably about 2 to about 4 carbon atoms in the chain.

"Branched alkenyl" means that one or more lower alkyl or alkenyl groups such as methyl, ethyl or propyl are attached to a linear alkenyl chain. "Lower alkenyl" means about 2 to about 4 carbon atoms in the chain, which may be straight or branched. The alkenyl group may be substituted by one or more halogen atoms. Exemplary alkenyl groups include ethenyl, propenyl, n-butenyl, i-butenyl, 3-methylbut-2-enyl, n-pentenyl, heptenyl, octenyl, cyclohexyl-butenyl and decenyl.

"Aryloxy" means an aryl-O— group wherein the aryl group is as defined herein. Exemplary groups include phenoxy and 2-naphtyloxy.

"Aryloxycarbonyl" means an aryl-O—CO— group wherein the aryl group is as defined herein. Exemplary aryloxycarbonyl groups include phenoxy-carbonyl and naphtoxycarbonyl.

"Arylcarbonyl" refers to an aryl-CO— group wherein the aryl group is as defined herein.

Exemplary arylcarbonyl group includes benzoyl.

The ($C_6$-$C_{10}$) aryl, ($C_3$-$C_{12}$) cycloalkyl, ($C_3$-$C_{12}$) cycloalkenyl are optionally substituted by one or more "ring system substituents".

"Ring system substituents" mean substituents attached to aromatic or non-aromatic ring systems, inclusive of halogen atoms, an optionally halogenated ($C_1$-$C_5$) alkyl, or an optionally halogenated ($C_1$-$C_5$)alkoxy, halogen, alkyl and alkoxy being as defined herein, The wording "in which the aryl, cycloalkyl and cycloalkenyl parts are optionally substituted by a halogen atom, by an optionally halogenated ($C_1$-$C_5$)alkyl or by an optionally halogenated ($C_1$-$C_5$)alkoxy" means that the aryl, cycloalkyl, cycloalkenyl groups are optionally substituted by one or more substituents selected from the group consisting of:

halogen atoms;

alkyl groups optionally substituted by one or more halogen atoms, and alkoxy groups optionally substituted by one or more halogen atoms.

The wording "optionally halogenated" means, in the context of the description, optionally substituted by one or more halogen atoms.

Preferably, each of R independently represents a halogen atom, an optionally substituted halogenated ($C_6$-$C_{10}$) arylcarbonyl, an optionally halogenated ($C_1$-$C_{18}$) alkyl, an optionally halogenated ($C_1$-$C_{18}$) alkoxy, or an optionally halogenated ($C_6$-$C_{10}$) aryl.

More preferably, R represents a ($C_1$-$C_{18}$) alkoxy group, more preferably a ($C_1$-$C_4$) alkoxy group and, most preferably, a methoxy group.

Preferably, p is 1 or 2 and more preferably 1.

R may be located in ortho (6), meta (3 or 5) and para (4) position on the phenyl ring with regard to the methoxy ethenyl group, preferably in meta position, more preferably at position 5.

Preferably, $R_1$ and $R_2$ represent independently a ($C_1$-$C_4$) alkyl group, and more preferably methyl, ethyl or isopropyl.

In another preferred embodiment, $R_1$ and $R_2$ form together a —$(CH_2)_n$— chain in which n represents 2 or 3.

According to the invention, a preferred embodiment is the compound of formula (I) in which R1 and R2 both represent a $C_2H_5$— group or form together a —$CH_2$—$CH_2$— group.

Preferred compounds of formula (I) can be selected from the group consisting in:
1) E,Z-1-methoxy-2-(2-(2-methyl-2-(1,3-dioxolan-2-yl)propoxy-)-5-bromo-phenyl)-ethene
2) E,Z-1-methoxy-2-(2-(2-methyl-2-(1,3-dioxolan-2-yl)propoxy-)-3-methoxy-phenyl)-ethene
3) E,Z-1-methoxy-2-(2-(2-methyl-2-(1,3-dioxolan-2-yl)propoxy-)-4,5-dichloro-phenyl)-ethene
4) E,Z-1-methoxy-2-(2-(2-methyl-2-(1,3-dioxolan-2-yl)propoxy-)-5-fluoro-phenyl)-ethene
5) E,Z-1-methoxy-2-(2-(2-methyl-2-(1,3-dioxolan-2-yl)propoxy-)-5-(para-chlorobenzoyl)-phenyl)-ethene
6) E,Z-1-methoxy-2-(2-(2-methyl-2-(1,3-dioxolan-2-yl)propoxy-)-5-trifluoro-methyl-phenyl)-ethene
7) E,Z-1-methoxy-2-(2-(2-methyl-2-(1,3-dioxolan-2-yl)propoxy-)-5-fluoro-2-phenyl)-ethene
8) E,Z-1-methoxy-2-(2-(2-methyl-2-(1,3-dioxolan-2-yl)propoxy-)-5-chloro-phenyl)-ethene
9) E,Z-1-methoxy-2-(2-(2-methyl-2-(1,3-dioxolan-2-yl)propoxy-)-4,5-dimethoxy-phenyl)-ethene
10) E,Z-1-methoxy-2-(2-(2-methyl-2-(1,3-dioxolan-2-yl)propoxy-)-5-phenyl-phenyl)-ethene
11) E,Z-1-methoxy-2-(2-(2-methyl-2-(1,3-dioxolan-2-yl)propoxy)-phenyl)-ethene
12) E,Z-1-methoxy-2-(2-(2-methyl-2-(1,3-dioxolan-2-yl)propoxy-)-5-methoxy-phenyl)-ethene.
13) E,Z-1-methoxy-2-(2-(2,2-dimethyl-3,3-diethoxy)propoxy-)-5-bromo-phenyl)-ethene
14) E,Z-1-methoxy-2-(2-(2,2-dimethyl-3,3-diethoxy)propoxy-)-3-methoxy-phenyl)-ethene
15) E,Z-1-methoxy-2-(2-(2,2-dimethyl-3,3-diethoxy)propoxy-)-4,5-dichloro-phenyl)-ethene
16) E,Z-1-methoxy-2-(2-(2,2-dimethyl-3,3-diethoxy)propoxy-)-5-fluoro-phenyl)-ethene
17) E,Z-1-methoxy-2-(2-(2,2-dimethyl-3,3-diethoxy)propoxy-)-5-(para-chlorobenzoyl)-phenyl)-ethene
18) E,Z-1-methoxy-2-(2-(2,2-dimethyl-3,3-diethoxy)propoxy-)-5-trifluoro-methyl-phenyl)-ethene
19) E,Z-1-methoxy-2-(2-(2,2-dimethyl-3,3-diethoxy)propoxy-)-5-fluoro-2-phenyl)-ethene
20) E,Z-1-methoxy-2-(2-(2,2-dimethyl-3,3-diethoxy)propoxy-)-5-chloro-phenyl)-ethene
21) E,Z-1-methoxy-2-(2-(2,2-dimethyl-3,3-diethoxy)propoxy-)-4,5-dimethoxy-phenyl)-ethene
22) E,Z-1-methoxy-2-(2-(2,2-dimethyl-3,3-diethoxy)propoxy-)-5-phenyl-phenyl)-ethene
23) E,Z-1-methoxy-2-(2-(2,2-dimethyl-3,3-diethoxy)propoxy)-phenyl)-ethene
24) E,Z-1-methoxy-2-(2-(2,2-dimethyl-3,3-diethoxy)propoxy-)-5-methoxy-phenyl)-ethene.

According to a particularly advantageous embodiment of the invention, a preferred compounds is a compound in which R=5-$OCH_3$, p=1 and R1 and R2 both form a —$CH_2$—$CH_2$— group (formula (IA)).

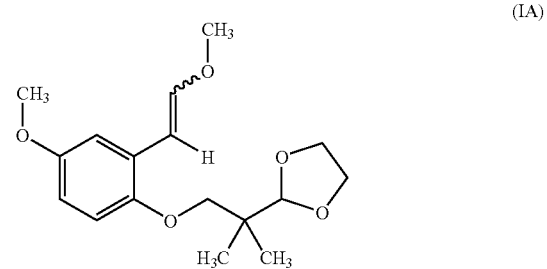

(IA)

According to a particularly advantageous embodiment of the invention, a preferred compound is in which R=7-$OCH_3$, p=1 and R1=R2=$C_2H_5$— (formula (IB)).

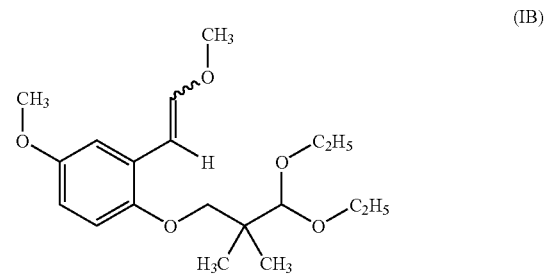

(IB)

Method for Preparing Compounds of Formula (II) Starting from Compounds of Formula (I)

According to the invention, the compounds of formula (I) are used for the preparation of compounds of formula (II) according to scheme 2:

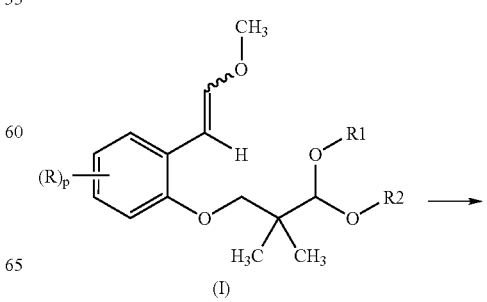

Scheme 2

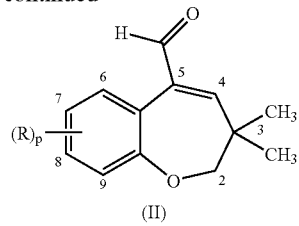

(II)

Thus, in another aspect, the present invention is directed to a method for preparing compounds of formula (II), comprising:
a) reacting the compound of formula (I) with an acid; and optionally
b) isolating the obtained compound of formula (II).

The conversion of the compound of formula (I) into the compound of formula (II) is carried out in the presence of an acid. The acid acts as a catalyzing agent. There is no particular restriction on the nature of the acid used in this reaction and any acid conventionally used in a reaction of this type may equally be used here, provided that it has no adverse effect on other parts of the molecule.

Suitable acids for catalyzing the cyclization reaction in step i) include inorganic acids such as chlorhydric acid, sulfuric acid, nitric acid and phosphoric acid; sulfonic acids such as methanesulfonic acid, ethane-sulfonic acid, benzenesulfonic acid and p-toluenesulfonic acid.

Inorganic acids are most preferred, and notably sulfuric acid.

The amount of acid is for example 0.2 to 2 moles and more preferably 0.5 to 1 moles relative to 1 mole of compound (I).

There is no particular restriction on the nature of the solvent to be employed, provided that it has no adverse effect on the reaction or on the reagent involved.

Suitable solvents for step a) are polar and aprotic solvents such as acetonitrile, N-methylpyrrolidone, N,N-dimethylformamide (DMF) and dimethylsulfoxide (DMSO), DMF being particularly preferred.

The reaction can take place over a wide range of temperatures, and the precise reaction temperature is not critical to the invention. In general, it has been found convenient to carry out the reaction at a temperature from about room temperature to about 100° C. and preferably from about 50° C. to 100° C.

The time required for the reaction may also vary widely, depending on many factors, notably the reaction temperature and the nature of the reagents. However, provided that the reaction is effected under the preferred conditions outlined above, a period from about 3 hours to about 20 hours will usually be sufficient.

The compounds thus prepared may be recovered from the reaction mixture by conventional means, for example the compounds may be recovered by distilling of the solvent from the reaction mixture or, if necessary, after distilling of the solvent from the reaction mixture, pouring the residue into water, followed by extraction with a water-immiscible organic solvent and distilling of the solvent from the extract. Additionally, the product can, if desired, be further purified by various well known techniques, such as recrystallization, reprecipitation or the various chromatography techniques, notably column chromatography or preparative thin layer chromatography.

Preferred compounds of formula (II) which may conveniently be prepared staring from corresponding compounds of formula (I) according to the present invention can be chosen from the group consisting in:

3,3-dimethyl-5-formyl-7-bromo-2,3-dihydrobenzoxepine, 3,3-dimethyl-5-formyl-9-methoxy-2,3-dihydrobenzoxepine, 3,3-dimethyl-5-formyl-7,8-dichloro-2,3-dihydrobenzoxepine, 3,3-dimethyl-5-formyl-7-fluoro-8-chloro-2,3-di-hydrobenzoxepine, 3,3-dimethyl-5-formyl-7-(para-chlorobenzoyl)-2,3-dihydrobenzoxepine, 3,3-dimethyl-5-formyl-7-trifluoromethyl-2,3-di-hydrobenzoxepine, 3,3-dimethyl-5-formyl-7-fluoro-2,3-dihydrobenzoxepine, 3,3-dimethyl-5-formyl-7-chloro-2,3-dihydrobenzoxepine, 3,3-dimethyl-5-formyl-7,8-dimethoxy-2,3-dihydro-benzoxepine, 3,3-dimethyl-5-formyl-7-phenyl-2,3-dihydrobenzoxepine, 3,3-dimethyl-5-formyl-2,3-dihydrobenzoxepine, 3,3-dimethyl-5-formyl-7-methoxy-2,3-dihydrobenzoxepine.

Method for Preparing the Compounds of Formula (I)

The compounds useful according to the invention may be prepared by the application or adaptation of known methods, by which are meant methods used heretofore or described in the literature, for example those described by R. C. Larock in *Comprehensive Organic Transformations*, VCH Publishers, 1989.

In another aspect, the invention relates to a method for preparing the compound of formula (I) comprising:
ii) reacting an aldehyde (V) resulting from step i) with a phosphorus ylid prepared from the reaction of a phosphonate (XIIa) or phosphonium salt (XIIb) with a base,

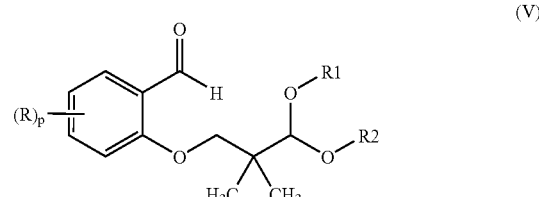

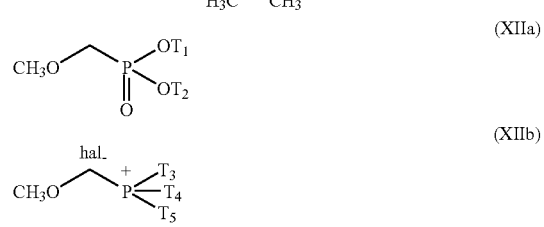

$T_1$ and $T_2$ represent independently $(C_1-C_5)$ alkyl, $T_3$, $T_4$, $T_5$ represent independently $(C_1-C_5)$ alkyl or $(C_6-C_{10})$ aryl, and optionally iii) isolating the obtained compound of formula (I).

Preferably, the aldehyde (V) is prepared by:
i) reacting a compound of formula (III) with a compound of formula (IV) in the presence of a base

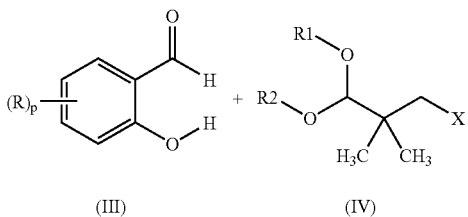

wherein R, $R_1$, $R_2$ and p are as defined hereabove, X represents an halogen atom, a ($C_6$-$C_{10}$) arylsulfonyloxy, a ($C_1$-$C_6$) alkylsulfonyloxy.

"Arylsulfonyloxy" means an aryl-$SO_2$— group wherein the group aryl is as defined herein. Examples of arylsulfonyloxy groups include the tosyl group of formula p-$CH_3$ ($C_6H_5$)—$SO_3$—.

"Alkylsulfonyloxy" means an alkyl-$SO_2$— group wherein the group alkyl is as defined herein. Examples of alkylsulfonyloxy group include the mesyl group of formula $CH_3$—$SO_3$—.

This synthetic route is illustrated in scheme 3:

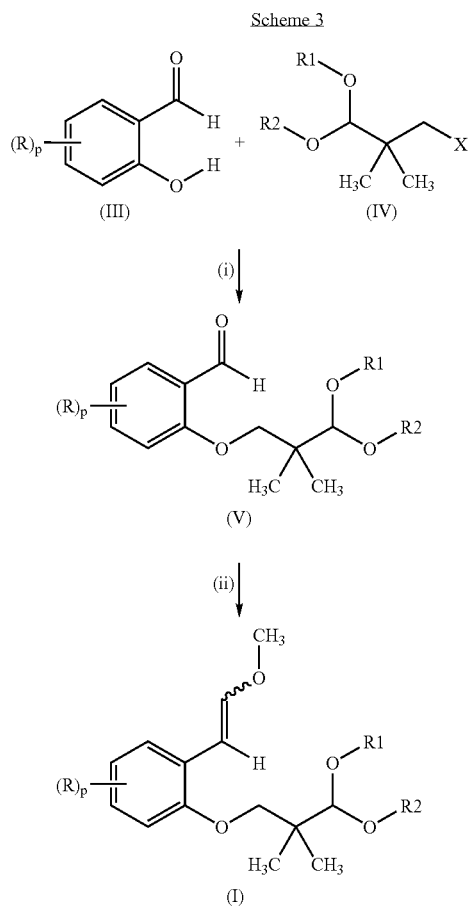

Step i)

The reaction of step i) is carried out in the presence of a base. There is no particular restriction on the nature of the base to be used in this reaction, and any base conventionally used in reactions of this type may equally be used here, provided that it has no adverse effect on other parts of the molecule.

Examples of suitable basis include alkali metal hydrides such as sodium hydride and potassium hydride; ($C_1$-$C_{10}$) alkyllithium compounds such as methyllithium and butyllithium, and alkali metal alkoxides, such as sodium methoxide and sodium ethoxide, and alkali metal carbonates, such as potassium carbonate and sodium carbonate. Of these, the alkali metal carbonates are particularly preferred.

The amount of base is for example 2 to 10 moles and preferably 2 to 3 moles relative to 1 mole of compound III.

There is no particular restriction on the nature of the solvent to be used, provided that is has no adverse effect on the reaction or on the reagent involved.

Examples of suitable solvents include hydrocarbons, which may be aromatic, aliphatic or cycloaliphatic hydrocarbons, such as hexane, cyclohexane, benzene, toluene and xylene; aprotic polar solvents such as N,N-dimethylformamide, N-methylpyrrolidone, dimethylsulfoxide. Of these, toluene, N-methylpyrrolidone, dimethylformamide and dimethylsulfoxide are particularly preferred.

The reaction can take place over a wide range of temperatures, and the precise reaction temperature is not critical to the invention. In general, it has been found convenient to carry out the reaction at a temperature of from about room temperature (20° C.) to 150° C., and more preferably of from 50° C. to 100° C.

The molar ratio of compound (IV) relative to compound (III) may vary from 1.0 to 1.5 equivalent, preferably from 1.05 to 1.1.

Step ii)

The reaction implemented in stage ii) is either a Wittig reaction or a Horner-Emmons/Wadsworth-Emmons reaction. These reactions are both well-known in the art and typically involve the preparation of a reactive ylid. For any further information on that subject, reference may be made to G. Wittig, U. Schöllkopf, Ber. 87, 1318 (1954); G. Wittig, W. Haag, ibid. 88, 1654 (1955); L. Horner et al., Ber. 91, 61 (1958); idem et al., ibid. 92, 2499 (1959); W. S. Wadsworth, Jr., W. D. Emmons, J. Am. Chem. Soc. 83, 1733 (1961).

When the ylid is prepared from a phosphonium salt (compound XIIb), the reaction implemented is a Wittig reaction.

When the ylid is prepared from a phosphonate (compound XIIa), the reaction is called a Horner-Emmons or Wadsworth-Emmons reaction.

At stage ii), the ylid is prepared by reacting a base either with a compound (XIIa) or with a compound (XIIb). The base used has to be sufficiently strong to remove an hydrogen atom in the alpha-position of the phosphorus.

Typically, the base is selected from the group consisting of alkali metal hydrides, alkali metal carbonates, alkali metal amides, ($C_1$-$C_{10}$) alkyllithium, and alkali metal alkoxides.

In the context of the invention, alkali metal hydrides such as sodium hydride and potassium hydride, and alkali metal alkoxides such as sodium methoxide, sodium ethoxide and potassium tert-butoxide are particularly preferred.

The reaction of the base on the compounds (XIIa) or (XIIb) is effected in a solution, preferably in an aprotic solvent, and notably in a solvent able to dissolve the phosphonate (XIIa) and respectively the phosphonium salt (XIIb).

Examples of suitable solvents are notably aprotic solvents, such as aromatic hydrocarbons, as for example benzene and toluene, ethers, such as diethylether, dioxane or tetrahydrofuran; aprotic polar solvents such as N,N-dimethylformamide, dimethylsulfoxide, N-methylpyrrolidone or HMPT and mixtures thereof.

The reaction of step ii) can take place over a wide range of temperatures, depending on the acidity of the compound (XIIa), respectively (XIIb), which means the ability to remove the hydrogen atom on the alpha-position with regard to the phosphorus. The type of the base used directly influences the choice of the reaction temperature. Thus, the stronger the base is, the lower the reaction temperature is.

When the base is an alkali metal alkoxide, a temperature comprised between −10° and 100° C. is generally suitable.

A stoichometric amount of basis is generally required in step ii) to convert the phosphonate or the phosphonium salt into the corresponding ylid. However, a slight excess of base may be used to ensure the total conversion of the compounds (XIIa) or (XIIb) into the ylid. Thus, the molar ratio of the base relative to the compound (XIIa), respectively (XIIb), is maintained between 1 and 1.2, preferably between 1 and 1.1, and more preferably between 1 and 1.05. The concentration of the compound (XIIa), respectively (XIIb), in the reaction mixture is not critical according to the invention. The concentration may vary between 0.01 mol/L and 10 mol/L, preferably between 0.1 and 1 mol/L.

According to a preferred embodiment, the ylid resulting from the reaction of the compound (XIIa), respectively (XIIb), with a base is performed before adding the aldehyde (V).

Preferably, the phosphorus ylid is prepared from a phosphonium salt (XIIb), more preferably from $CH_3OCH_2PPh_3Cl$.

According to a preferred embodiment, the ylid is prepared by reacting $CH_3OCH_2PPh_3Cl$ with potassium tert-butoxide in tetrahydrofuran.

Compounds of Formula (IV)

In another aspect, the invention relates to compounds of formula (IV):

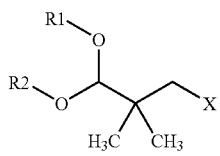

(IV)

wherein X represents an halogen atom, a $(C_1-C_6)$ alkylsulfonyloxy or a $(C_6-C_{10})$ arylsulfonyloxy, $R_1$, $R_2$ are a $(C_1-C_{18})$ alkyl group or form together a —$(CH_2)_n$—, wherein n represents 2, 3 or 4, with the exclusion of the compounds of formula (IV), wherein X=I and $R_1=R_2=CH_3$; X=I, Br or $pCH_3$—$(C_6H_5)SO_3$—, and $R_1$ and $R_2$ form together a —$(CH_2)_3$— chain.

Preferred compounds of formula (IV) are notably those wherein

—$R_1$, $R_2$ represents a $(C_2-C_6)$ alkyl group or form together a —$(CH_2)_2$— or —$(CH_2)_4$— chain; and/or —X represents Cl, Br, I or $CH_3SO_3$—.

Most preferred compounds are notably the compounds of formula (IV) wherein:

X represents Cl, Br, I, $CH_3SO_3$— and/or $R_1=R_2=C_2H_5$ or $R_1$ and $R_2$ form together a —$(CH_2)_2$— chain.

The compounds of formula (IV) are particularly useful for preparing the compounds of formula (I) and, as a result, are also advantageous synthetic intermediates for the preparation of the compounds of formula (II).

Step iii)

The compounds of formula (I) thus prepared may be recovered from the reaction mixture by conventional means, for example the compounds may be recovered by distilling of the solvent from the reaction mixture or, if necessary, after distilling of the solvent from the reaction mixture, pouring the residue into water, followed by extraction with a water-immiscible organic solvent and distilling of the solvent from the extract. Additionally, the product can, if desired, be further purified by various well known techniques, such as recrystallization, reprecipitation or the various chromatography techniques, notably column chromatography or preparative thin layer chromatography.

Methods for Preparing of the Compound of Formula (IV)

The compounds of formula (IV) according to the present invention may be prepared by the application or adaptation of known methods, by which are meant methods used heretofore or described in the literature, for example those described by R. C Larock in *Comprehensive Organic Transformations*, VCH Publishers, 1989.

In another aspect, the invention is directed to a method for preparing the compound of formula (IV).

The compound of formula (IV) may be prepared by the method comprising the steps of:

b1) reacting an aldehyde (VII) with alcohols $R_1OH$ and $R_2OH$ or HO—$(CH_2)_n$—OH, in the presence of an acid, wherein n, $R_1$ and $R_2$ are as defined hereabove;

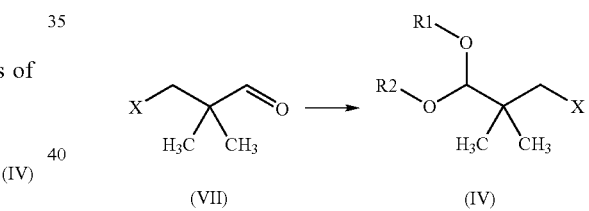

(VII)          (IV)

and optionally c1) isolating the resulting compound (IV).

Preferably, the aldehyde (VII) is prepared by:

a1) oxidizing an alcohol of formula (VI) into the corresponding aldehyde (VII);

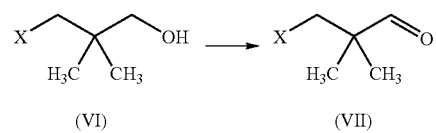

(VI)          (VII)

wherein X represents an halogen atom, a $(C_6-C_{10})$ arylsulfonyloxy group, a $(C_1-C_6)$ alkylsulfonyloxy group.

Step a1)

Conventional oxidizing agents may be used in accordance with standard practice to convert primary alcohols into aldehydes. Precautions must however be taken so that the aldehyde is not further oxidized to the carboxylic acid. For further information on that subject, reference may be made to March's, *Advanced Organic Chemistry*, Michael B. Smith and Jerry March.

Suitable oxidizing agents include DMSO, chromate salts such as pyridinium dichromate, $Na_2Cr_2O_7$, $K_2Cr_2O_7$, $Cr_3$ and NCS/tempo and tempo/NaOCl.

Different solvents may be used provided that they have no adverse effect on the reaction or on the reagent involved.

Examples of suitable solvents are notably halogenated hydrocarbons such as dichloromethane, 1,2-dichloroethane, chloroform.

According to a preferred embodiment, the alcohol (VI) is oxidized by tempo/NaOCl in dichloromethane, in similar conditions than those disclosed in the publication J. Jurczak et al., *Tetrahedron* (1998), vol. 54, p. 6051-6064.

Preferably, the group X of the compound (VI) represents a iodine atom.

Such compounds may be prepared from the corresponding compound of formula (IV), wherein X=Cl, Br or alkylsulfonyloxy, according to conventional methods,.

As an example, the compound of formula (VI), wherein X=Cl, may be converted into X=I in the presence of NaI in DMF.

Step b1)

The acids which can be used in step b1) may be any conventional acid used for the protection of aldehydes under the form of a ketal.

Suitable acids include notably chlorhydric acid, sulfuric acid, nitric acid and phosphoric acid ; sulfonic acids such as methan sulfonic acid, ethane sulfonic acid, benzene sulfonic acid and paratoluene sulfonic acid. Of these, sulfonic acid and notably paratoluene sulfonic acid are particularly preferred.

The molar ratio of acid is for example 0.001 to 0.5 equivalents, more preferably 0.01 to 0.1 equivalents relative to the aldehyde VII.

The molar ratio of the alcohols $R_1OH$ and $R_2OH$, or HO—$(CH_2)_n$—OH may vary from 1.0 to 2.0 equivalents relative to the aldehyde VII, more preferably from 1.0 to 1.1 inclusive.

In a preferred embodiment, the alcohol is HO—$(CH_2)_n$—OH, and more preferably ethylene glycol.

As an example, this preferred embodiment of preparation is illustrated by the preparation of the compound (IVA) according to scheme 5.

The compounds of formula (IV) may also be prepared by the method comprising the steps of:

a2) reacting an aldehyde of formula (VIII) with a formaldehyde of formula (IX) in the presence of a base and an acid;

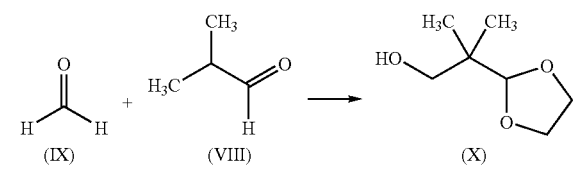

b2) converting the alcohol function of the compound (X) into an halogen atom or a ($C_1$-$C_{16}$) alkylsulfonyloxy group or a ($C_6$-$C_{10}$) arylsulfonyloxy group; and optionally c2) isolating the product obtained.

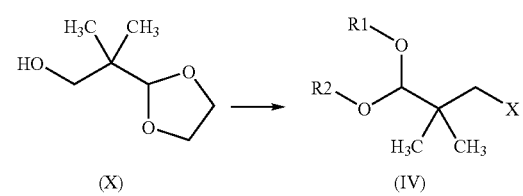

Step a2)

The preparation of compounds (X) in step a2) may be effected according to Tsuzuki et al., *Tetrahedron Letters,* Vol. 19, No. 11, p. 989-992 (1978) and Matsuda et al., *Tetrahedron* (46(10), p. 3469-3488, (1990)). Analogues have been described by L. Paquette et al. (JACS 105(25), p. 7352-7358, (1983 )) and by M. H. Seo et al. (*J. of Korean Chem. Soc.,* 39(6), p. 489-491 (1995).

Step b2)

The reaction of step b2) may be effected according to conventional methods.

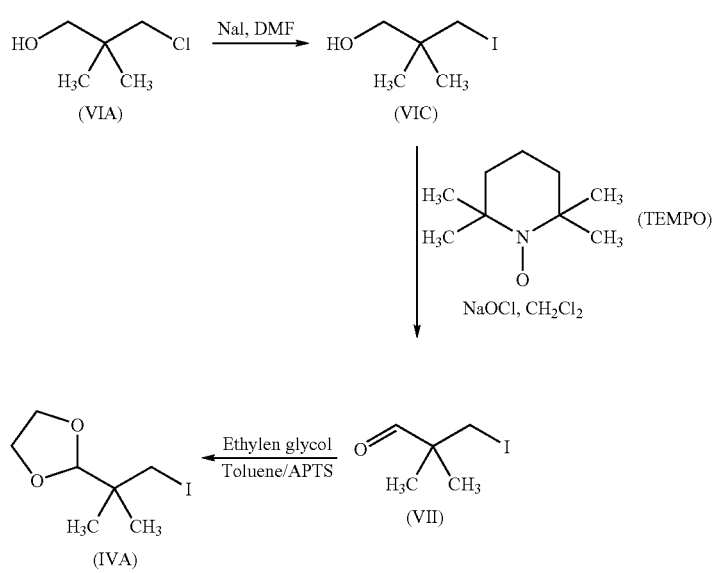

Preferably, the hydroxyl group of the compound (X) is converted into an alkylsulfonyloxy or arylsulfonyloxy group.

This conversion may be effected according to conventional methods such as reacting the compound (X) with an alkylsulfonyl or arylsulfonyl halide in the presence of a base.

Examples of suitable alkylsulfonyl or arylsulfonyl halides include notably alkyl or arylsulfonyl chloride or bromide such as methylsulfonyl chloride or p-toluenesulfonylchloride.

Examples of suitable bases include notably amines, preferably tertiary amines such as triethylamine, diisopropylethylamine.

Examples of suitable solvents include aprotic solvents, notably halogenated hydrocarbons such as dichloromethane, 1,2-dichloroethane.

This conversion of the hydroxyl group into an alkyl or arylsulfonyloxy group can take place over a wide range of temperatures, notably between $-10°$ C. and $100°$ C.

According to a preferred embodiment, the alkylsulfonyloxy or arylsulfonyloxy group is converted into an halogen atom.

Conventional methods may be used such as reacting the alkylsulfonyloxy or arylsulfonyloxy group with an alkali metal halide such as sodium iodide, sodium bromide, lithium chloride.

Suitable solvents for this reaction are notably aprotic solvents, in particular aprotic polar solvents such as N,N-dimethylformamide, N-dimethylsulfoxide acetonitrile.

As an example, this synthetic route is illustrated by the preparation of compound (IVA) in the following scheme 6.

Alternatively, the hydroxyl function of the compound (X) may be converted directly into an halogen atom, according to conventional methods.

Conventional methods include notably reacting the alcohol (X) with the $Me_3SiCl$ in DMSO, or $PPh_3$ in combination with $CCl_4$ or $CBr_4$.

For any further information regarding these methods, reference may be made to M. B. Smith and J. March, in March's *Advanced Organic Chemistry*, 5th edition, Wiley Interscience.

In the reactions described hereabove, it may be necessary to protect reactive functional groups, for example amino or carboxy groups, where these are desired in the final product, to avoid their unwanted participation in the reactions. Conventional protecting groups may be used in accordance with standard practice, for example see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The starting materials are commercially available or may be prepared by the application or adaptation of known methods.

The compounds of the invention, their methods of preparation will appear more clearly form the examination of the following examples, which are presented as an illustration only and are not to be considered as limiting the invention in its scope.

EXAMPLES

Example 1

3-iodo-2,2-dimethyl-1-propandioxolane (Formula (IVA))

A) Preparation According to Scheme 5:

a) 3-iodo-2,2-dimethyl-propanol (Formula (VI): X=I (VIC))

80 g (0.53 mol) of dry NaI and 5 g (0.03 mol) of $K_2CO_3$ are added under argon to a solution of 50 g (0.4 mol) of 3-chloro-2,2-dimethyl-1-propanol (formula VIA) in 75 ml of DMF. The mixture is stirred at reflux for 8 hours. The reaction mixture is subsequently brought to room temperature and diluted by addition of 500 ml of water. The organic phase is extracted with 1050 ml of ethyl acetate, washed with a saturated aqueous solution of $Na_2SO_3$, then with a 250 ml of a saturated solution of sodium bicarbonate dried over 60 g of anhydrous magnesium sulfate and evaporated to give crude compound of formula (VIC).

$H^1$RMN δ ppm: 0.97 (s,6H,$CH_3$); 2.48 (s, broad, OH); 3.17 (s, 2H, $CH_2$); 3.37 (s,2H, $CH_2$).

$^{13}$C RMN δ ppm: 20.3 ($CH_2$I); 23.7 (2C,$CH_3$); 35.5 (q, 1C); 69.7 ($CH_2$0)

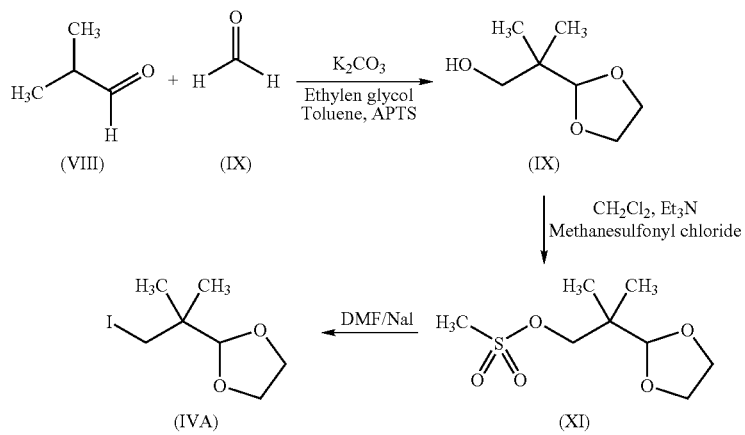

b) 3-iodo-2,3-dimethyl-1-propanal (Formula (VII)):
X=I (VIIA))

100 ml of water are added under argon to a solution of 75.25 g (0.35 mol) of the crude compound of formula VI in 300 ml of methylene chloride. Then 4.71 g (0.035 mol) of potassium bromide and 58.8 g of sodium bicarbonate are added to the mixture. After cooling at −5° C., 0.546 g of TEMPO are added and the mixture is strongly stirred for 30 mn. Then followed 275 ml of a solution of 10%-13% NaOCl (the reaction is controlled by TLC). The mixture is extracted with twice 250 ml of methylene chloride, washed with 400 ml of HCl 0.1N and then with 400 ml of a saturated solution of $Na_2SO_3$. The organic phase is dried over 5 g of sodium bicarbonate and evaporated. The organic oil is distilled at 30° C. under 400 mbar to give 58 g of crude compound of formula (VII).

$H^1$RMN: δ ppm: 1.19 (s,6H,$CH_3$); 3.21 (s, 2H, $CH_2$I); 9.38 (s, 1H, CHO).

$^{13}C$ RMN δ ppm: 12.5 ($CH_2$I); 22.1 (2C,$CH_3$); 45.3 (q,1C); 201.9 (CHO).

c) 3-iodo-2,2-dimethyl-1-propandioxolane (formula (IVA))

58 g of the crude compound of formula VI are mixed with 61 ml of ethylene glycol, 0.778 g of paratoluenesulfonic acid in 155 ml of toluene. The mixture is heated at reflux for 8 hours and 4-5 ml of water are eliminated. The solution is washed with a saturated solution of sodium bicarbonate and the organic phase is extracted with ethyl acetate (400 ml). After drying over sodium bicarbonate, the solvent is evaporated and the residue is distilled at 88-90° C. under 8-10 mbar to give 52 g of compound of formula (IVA). The overall yield for the 3 steps is 50%

$H^1$RMN: δ ppm: 1.01 (s,6H,$CH_3$); 3.20 (s, 2H, $CH_2$I); 3.81-3.97 (m,4H, $CH_2$dioxolane); 4.65 (s,1H, anomeric).

$^{13}C$ RMN δ ppm: 18.2 ($CH_2$I); 22.4 (2C,$CH_3$); 37.4 (q); 65.4 (2C, $CH_2$O).

IR(film) $cm^{-1}$: 950; 1111.2; 1473.4; 1681.0; 2881.2; 2974.9 MS m/z=257 [M+H].

B. Preparation According to Scheme 6:

a): 2-(2-hydroxy-1,1-dimethylethyl)-1,3-dioxolane (Formula(X))

To a stirred mixture of 100 g (1.4 mol) of isobutyraldehyde and 37% formaldehyde (150 g, 1.9 mole) was added 35 g (0.26 mol) of potassium carbonate by portions under cooling in an ice bath. The mixture is warmed to room temperature and stirred over night. The organic layers are separated in two phases on standing and extracted with 400 ml of toluene. The combined organic layers are dried over 20 g of anhydrous magnesium sulfate and concentrated in vacuo to give 152 g of an oil. This crude oil is solubilized in 300 ml of toluene containing 205 ml of ethylene glycol and 3.5 g of paratoluenesulfonic acid. The mixture is heated at reflux under a Dean-Stark for 6-7 hours. After cooling at room temperature, the mixture is diluted with 300 ml of toluene, washed with a saturated solution of sodium bicarbonate, dried and concentrated to give 152 g of a crude compound of formula (X).

b) 2-(2-methansulfonyloxy-1,1-dimethylethyl)-1,3-dioxolane (Formula (XI))

The crude compounds of formula X (152 g, 1.03 mol) are solubilized in 1.3 liter of methylene chloride containing 200 ml of $Et_3N$. The solution is cooled to 0° C. and 100 ml of methanesulfonyl chloride are added slowly. The mixture is then stirred for 30 minutes. 2.5 liters of water are added and the organic layer is extracted with methylene chloride, washed with a saturated solution of sodium bicarbonate, dried over sodium bicarbonate and concentrated in vacuo. The residue is then distilled at 110° C. under 0.1 mbar to give 150 g (yield: 66%) of compound of formula (XI).

$H^1$RMN: δ ppm: 0.96 (s,6H,$CH_3$); 2.96 (s, 3H, $CH_3$O); 3.73-3.83 (m,4H, $CH_2$ dioxolane);4.03 (s,2H, $CH_2$OMs); 4.63 (s,1H,anomeric).

IR(film) $cm^{-1}$: 842.2; 960; 1093; 1177 ($SO_2$); 1343 ($SO_2$); 1404.1; 1470; 2974

MS m/z=225 [M+H]

c) 3-iodo-2,2-dimethyl-1-propandioxolane (Formula (IVA))

148 g (0.6 mol) of compound of formula (XI) are solubilized in 700 ml of dimethylformamide containing 297 g (2 mol) of NaI. The mixture is stirred under reflux for 8 hours. 1 liter of a saturated solution of NaCl are added. The organic layer is extracted with ethyl acetate (2×800 ml), washed with a saturated solution of $Na_2SO_3$, and 200 ml of a saturated solution of sodium bicarbonate. After concentration and distillation at 85-92° C. under 10 mbar, 142 g of compound of formula (IVA) are obtained.

Yield: 84%.

Example 2

2-(2-methyl-2-(1,3-dioxolan-2-yl)propoxy-)-5-methoxy-benzaldehyde (Formula (V): p=1; R=5-$CH_3$O; R1,R2=—$CH_2$—$CH_2$—: (VA))

A mixture of 70 g (0.27 mol) of compound of formula (IVA), 67.89 g (0.57 mol) of potassium carbonate, 100 ml of 1-methyl-2-pyrrolidone, 67.89 g (0.57 mol), 25 g (0.16 mol) of 2-hydroxy-5-methoxy-benzaldehyde (formula (III)) is stirred at 132° C. for 3-4 hours. Then 25 g (0.16 mol) of 2-hydroxy-5-methoxy-benzaldehyde solubilized in 25 ml of 1-methyl-2-pyrrolidone are added and the mixture is stirred at 132° C. for 4 hours. 1 liter of a saturated solution of NaCl is then added followed by 500 ml of water. The mixture is extracted with 1 liter of diisopropyl ether. The organic phase is washed with a solution of NaOH 15%, dried over sodium bicarbonate and concentrated in vacuo to give 84 g of crude compound (VA).

Yield of crude product: 100%.
Yield: 88% after purification with bisulfite.

Example 3

E,Z-1-methoxy-2-(2-(2-methyl-2-(1,3-dioxolan-2-yl) propoxy-)-5-methoxy-phenyl)-ethene (Formula (I): p=1; R=5-$CH_3$O; R1,R2=—$CH_2$—$CH_2$—: (IA))

1.6 g (14.28 mmol) of potassium terbutylate are added at −5° C. to a solution of 2.9 g (8.57 mmol) of [$CH_3OCH_2P(Ph)_3$]$^+Cl^-$ in 20 ml of THF. The mixture is stirred at 23° C. for 2 hours. Then 2 g (7.14 mmol) of aldehyde (VA) are added. The mixture is stirred at room temperature for 2 additional hours. 10 ml of a cold (ice) saturated solution of ammonium chloride are added. The organic phase is extracted with 350 ml of diethyl ether. After drying over potassium carbonate and concentration, the residue is purified by chromatography H$^1$RMN: δ ppm: 1.06 and 1.07 (s,6H,2CH$_3$); 3.67 (s, 2H, CH$_2$O); 3.72 and 3.74 (s,3H,CH$_3$O);3.75 (s,3H,CH$_3$O); 3.85-3.94 (m,4H, CH$_2$ dioxolane), 4.85 (s,1H, anomeric); 5.63 (d,0.3H, J=6HZ,CH=); 6.03 (d,0.7H, J=14HZ,CH=); 6.15 (d,J=8HZ,CH=); 6.58-6.80 (m,2.7H,CH=); 7.12 (d,0.7H, J=12HZ,CH=); 7.64 (d,0.3H,J=2HZ,CH=).

IR(film)cm$^{-1}$: 1049; 1111; 1222; 1464; 1497; 1641;2966
MS m/z=309 [M+H]
Yield: 94%.

Example 4

3,3-dimethyl-5-formyl-7-methoxy-2,3-dihydrobenzoxepine (Formula (II): p=1; R=7-CH$_3$O; (IIA))

To a solution of 180 g (0.58mol) (IA) in 4 liters of dimethylformamide is added 1.7 liter of 28% sulphuric acid. The temperature goes up to 70° C. After cooling to 35-40° C., the mixture is then heated at 75° C. for 16 hours. The mixture is cooled to room temperature. 3 liters of water are added and the organic phase is extracted with ethyl acetate. After washing with a saturated solution of sodium bicarbonate (pH should be between 6 and 8) and drying over magnesium sulphate, the solvent is evaporated in vacuo and the residue purified by chromatography. After purification, the compound obtained is identical to the compound obtained in example 16 i) of [EP 1140893 B1, yield: 96%].
Yield: 100%.

Example 5

3-bromo-2,2-dimethyl-1-propandioxolane(Formula (IV): X=Br, R$_1$ and R$_2$ are —CH$_2$—CH$_2$-(IVB))

To a solution of 4 g (20 mmol) of 3-bromo-2,2-dimethyl-propanol (formula (VI): X=Br (VIA)), 1 g of molecular sieves (4OA) in 50 ml dichloromethane cooled to 0° C., are added 6 g (30 mmol) of pyridinium chlorochromate (PCC) on Celite (50/50). After 30 minutes, the solvent is evaporated and the crude residue (aldehyde of formula (VII)) is extracted with diethyl ether. After concentration at 17° C. under 75 mbar, the residue is treated according to example 1 A) c) and distilled at 68° C. under 2.5 mbar to give compound (IVB).

H$^1$RMN: δ ppm: 0.99 (s,6H,2CH$_3$); 3.35 (s, 2H, CH$_2$Br); 3.78-3.94 (m,4H,CH$_2$O); 4.69(s,1H, anomeric)

$^{13}$C RMN δ ppm: 21.3 (2C,CH$_3$); 38.5 (q); 65.8 (2C, CH$_2$O); 107.8 (anomeric).
IR(film) cm$^{-1}$: 1001; 1474; 2883; 2970.
[Yield: N]

Example 6

1-chloro-2,2-dimethyl-3,3-diethoxy-propane (Formula (IV): X=Cl, R$_1$=R$_2$=CH$_3$CH$_2$— (IVC))

A solution of 6.76 ml (77.5 mmol) de (COCl)$_2$ in 220 ml of dry dichloromethane is cooled to −40° C. Then 153.8 ml (10.9 mmol) of dimethylsulfoxide are added slowly. 5 minutes later, a solution of 7.5 g of 1-chloro-2,2-dimethyl-propanol (formula (VIC): X=Cl) in 61 ml of dichloro-methane is added. The mixture is stirred for 15 minutes followed by the addition of 36 ml (264.3mmol) de Et$_3$N. 30 ml of dichloromethane are added and the mixture is warmed to room temperature. The organic phase is washed with water (3×150 ml), dried over sodium sulfate, concentrated in vacuo (17° C./75 mbar). The oil obtained is solubilized in ethanol and the solution is heated under reflux with a catalytic amount of PTSA for 120 minutes, concentrated in vacuo (19° C./32 mbar). After distillation at 62-65° C. under 10 mbar, 8 g of compound (IVC) are obtained (yield: 68%).

H$^1$RMN δ ppm: 0.96 (s,6H, 2CH$_3$); 1.25 (t, 6H,J=8HZ; OCH$_2$CH$_3$); 3.44(s,2H,CH$_2$Cl); 3.48-3.57 (m,2H,CH$_2$O); 3.75-3.88 (m,2H, CH$_2$O); 4.25 (s,1H,anomeric)

$^{13}$C RMN δ ppm: 15.4 (2C,CH$_3$); 20.4 (2C, OCH$_2$CH$_3$); 41.4 (q);53.1 (CH$_2$Cl);65.8 ((2C, OCH$_2$CH$_3$); 107.7 (anomeric).
IR(film) cm$^{-1}$: 656; 1063; 1249; 1381;1474;
MS m:z=159

Example 7

1-bromo-2,2-dimethyl-3,3-diethoxy-propane (Formula (IV): X=Br, R$_1$=R$_2$=CH$_3$CH$_2$— (IVD))

Prepared according to example 6; boiling point: 74-78° C. under 10 mbar

H$^1$RMN: δ ppm: 0.92 (s,6H,2CH$_3$); 1.12 (t,6H,J=6HZ; OCH$_2$CH$_3$); 3.28(s,2H,CH$_2$Cl); 3.42-3.53 (m,2H,CH$_2$O); 3.65-3.80 (m,2H, CH$_2$O); 4.17 (s,1H,anomeric)

$^{13}$C RMN δ ppm: 15.2 (2C,CH$_3$); 21.0 (2C, OCH$_2$CH$_3$); 40.3 (q);43.4 (CH$_2$Br); 66.1 ((2C, OCH$_2$CH$_3$); 107.9 (anomeric).
IR(film) cm$^{-1}$: 656; 1063; 1249; 1381;1474;
MS m:z=159
Yield: 79%.

Example 8

1-methanesulfonyloxy-2,2-dimethyl-3,3-diethoxy-propane (Formula (IV): X=CH$_3$SO$_3$, R$_1$=R$_2$=CH$_3$CH$_2$— (IVE))

A solution of 0.175 mol of 2,2-dimethyl-propanediol-1,3 in methylene chloride is cooled to −5° C.Then one equivalent of pyridine is added under inert atmosphere, followed 30 minutes later by one equivalent of methanesulfonyl chloride. The mixture is warmed to room temperature and stirred for one week. The solution is washed with 250 ml of HCl 0.1N, dried over magnesium sulfate, evaporated in vacuo to give 30 g of crude 2,2-dimethyl-1-methanesulfonyloxy-propanol (yield: 68%).

The crude alcohol is treated according to example 5 to give after distillation at 98° C. under 0.1 mbar the compound of formula (IVE).

H$^1$RMN: δ ppm: 0.89 (s,6H,2CH$_3$); 1.12 (t, 6H,J=6HZ; OCH$_2$CH$_3$); 2.90(s,3H,CH$_3$SO$_3$); 3.36-3.51 (m,2H,CH$_2$O); 3.65 3.80(m,2H,CH$_2$O); 3.95(s,2H,CH$_3$SO$_3$CH$_2$); 4.12(s, 1H,anomeric)

$^{13}$C RMN δ ppm: 15.2 (2C,CH$_3$); 19.2 (2C, OCH$_2$CH$_3$); 36.5 (CH$_3$SO$_3$);40.1 (q); 66.0 ((2C, OCH$_2$CH$_3$); 75.7 (CH$_3$SO$_3$CH$_2$); 107.7 (anomeric).
MS m:z=181

Example 9

2-(2,2-dimethyl-3,3-diethoxy-propoxy-)-5-methoxy-benzaldehyde (Formula (V) : p=1; R=5-CH$_3$O; R1,R2=CH$_3$CH$_2$O—: (VB))

Prepared according to example 2 from 2-hydroxy-5-methoxy-benzaldehyde (formula (III)) and compounds of examples 6 or 7 or 8 to give compound of formula (VB).

H[1]RMN: δ ppm: 1.05 (s,6H,2CH$_3$); 1.17 (t, 6H,J=6HZ; OCH$_2$CH$_3$); 3.47(m,2H,CH$_2$O); 3.76-4.88(m,7H); 4.33 (s,1H, anomeric); 6.93 (d,1H, J=10HZ,CH aromatic); 80(m, 2H,CH$_2$O); 3.95(s,2H,CH$_3$SO$_3$CH$_2$); 4.12 (s,1H,anomeric); 7.10 (dd,1H,J=4HZ,10HZ,CH aromatic); 7.29 (d,1H, J=4HZ,CH aromatic); 10.50 (s,1H,CHO)

[13]C RMN δ ppm: 15.4 (2C,CH$_3$); 19.9 (2C, OCH$_2$CH$_3$); 40.8 (q); 55.8 ((1C,OCH$_3$); 66.3 (2C,CH$_2$O); 75.07 (CH$_2$O);108.0 (anomeric); 110.0 (CH aromatic); 114.4 (CH aromatic); 123.7 (CH aromatic); 124.7 (q, CH aromatic); 153.5 (q, CH aromatic); 156.6 (q, CH aromatic); 189.4 (CHO).

IR(film)cm$^{-1}$: 1115; 1219; 1497; 1681;1686;2878;2975.

Example 10

E,Z-1-methoxy-2-((2,2-methyl-3,3-diethoxy)propoxy-)-5-methoxy-phenyl)-ethene (formula (I): p=1; R=5-CH$_3$O; R1,R2=CH$_3$CH$_2$O: (IB))

Prepared according to example 3 from compound of example to give compound of formula (IB)

H[1]RMN: δ ppm: 0.98 and 0.99 (s,6H,2CH$_3$); 1.07-1.15 (t, 6H,J=6HZ, OCH$_2$CH$_3$); 3.43 (m,2H,CH$_2$O);3.62-3.78 (m,10H,); 4.33 (s,1H, anomeric); 5.58(d,0.6H, J=8HZ,CH=); 5.97 (d, 0.4H, J=12HZ, CH=); 6.10 (d,0.6H, J=8HZ,CH=); 6.53-6.74 (m,2.4H); 7.05 (d,0.4H,CH=); 7.59(m,0.0.6H).

The invention claimed is:

1. A compound of general formula (I):

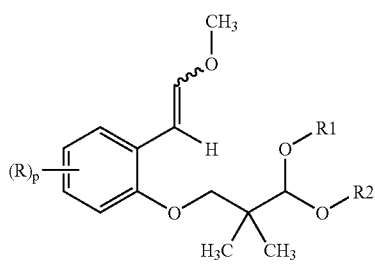

wherein
R is, in each case independently, (C$_1$-C$_{18}$)alkoxy;
p represents 0, 1, 2, 3 or 4;
R$_1$ and R$_2$ are each independently (C$_1$-C$_{18}$)alkyl or together form -(CH$_2$)$_n$-; and
n represents 2, 3 or 4.

2. A compound according to claim 1, wherein R is methoxy, ethoxy, isopropyloxy, butoxy, and hexyloxy.

3. A compound according to claim 1, wherein R represents methoxy.

4. A compound according to claim 1, wherein R represents 7-methoxy.

5. A compound according to claim 1, wherein p is 1.

6. A compound according to claim 1, wherein R$_1$ and R$_2$ represent independently a (C$_1$-C$_4$) alkyl group.

7. A compound according to claim 1, wherein R$_1$ and R$_2$ represent ethyl or form together a -CH$_2$-CH$_2$ - group.

8. A compound according to claim 1, wherein said compound is selected from Formulas IA and IB:

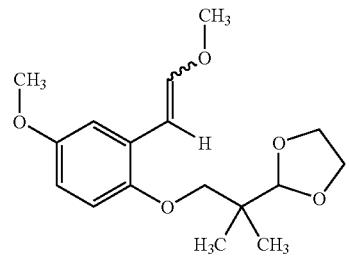

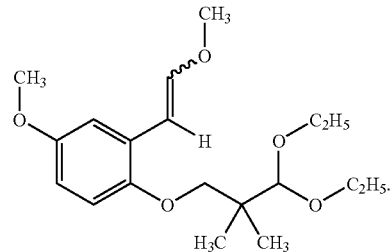

9. A method for preparing a compound of formula (I) according to claim 1, comprising:
ii) reacting an aldehyde (V) with a phosphorus ylid prepared from the reaction of a phosphonate (XIIa) or phosphonium salt (XIIb) with a base,

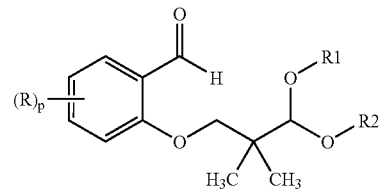

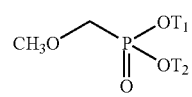

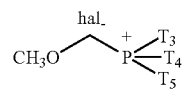

wherein
T$_1$ and T$_2$ represent independently (C$_1$-C$_5$)alkyl, and
T$_3$, T$_4$, T$_5$ represent independently (C$_1$-C$_5$) alkyl or (C$_6$-C$_{10}$)aryl, and
iii) optionally isolating the obtained compound of formula (I).

10. A method according to claim 9, wherein the aldehyde (V) is prepared by:
i) reacting a compound of formula (III) with a compound of formula (IV) in the presence of a base

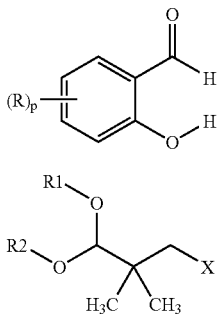

(III)

(IV)

wherein R, $R_1$, $R_2$ and p are as defined in formula (I), and X represents halogen, ($C_1$-$C_6$) alkylsulfonyloxy, ($C_6$-$C_{10}$) aryl-sulfonyloxy.

11. A method according to claim 9, wherein the phosphorus ylid of ii) is prepared by reacting a base on a phosphonium salt.

12. A method according to claim 9, wherein the base in ii) is an alkali metal hydride, an alkali metal carbonate, a ($C_1$-$C_{10}$) alkyllithium, or an alkali metal alkoxide.

13. A method according to claim 9, wherein ii) is performed in an aprotic solvent selected from aromatic hydrocarbons, ethers, polar aprotic solvents, and mixtures thereof.

14. A method according to claim 9, wherein the phosphorus ylid is prepared by reacting an alkali metal alkoxide with a phosphonium salt (XIIb) at a temperature of between $-10°$ and $100°$ C.

15. A method according to claim 10, wherein the base in i) is an alkali metal carbonate, alkali metal hydride, ($C_1$-$C_{10}$) alkylithium, or an alkali metal alkoxide.

16. A method according to claim 10, wherein i) is performed in an aprotic solvent selected from polar aprotic solvents, aromatic hydrocarbons or mixtures thereof.

17. A method according to claim 10, wherein the compound of formula (IV) is prepared by:
b1) reacting an aldehyde (VII) with alcohols $R_1$OH and $R_2$OH or HO—(CH$_2$)$_n$—OH, in the presence of an acid, wherein n, $R_1$ and $R_2$ are as defined in formula (I); and optionally

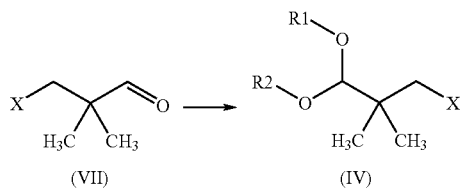

c1) isolating the resulting compound (IV).

18. A method according to claim 17, wherein the aldehyde of formula (VII) is prepared by:
a1) oxidizing the alcohol of formula (VI) into the corresponding aldehyde of formula (VII)

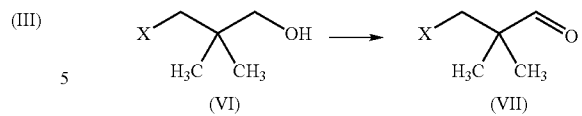

wherein X represents halogen, ($C_1$-$C_6$) alkylsulfonyloxy, ($C_6$-$C_{10}$)arylsulfonyloxy.

19. A method according to claim 18, wherein the alcohol of formula (VI) is oxidized by 2,2,6,6,-tetramethylpiperidinyloxy in combination with NaOCl.

20. A method according to claim 10, wherein the compound of formula (IV) is prepared by:
a2) reacting an aldehyde formula (VIII) with the formaldehyde (IX) in the presence of a base and an acid to obtain a hydroxyl compound of formula(X);

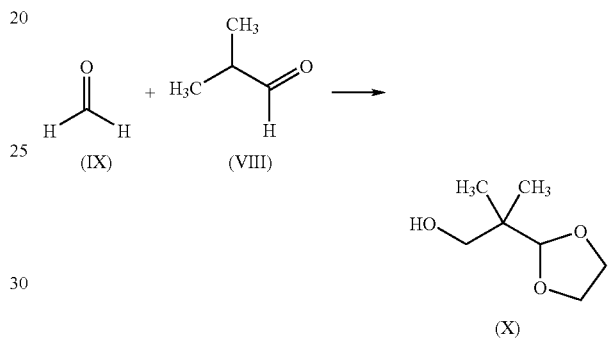

b2) converting the hydroxyl function of the compound (X) into an halogen atom, a ($C_1$-$C_6$) alkylsulfonyloxy group, or an ($C_6$-$C_{10}$) arylsulfonyloxy group; to obtain a compound of formula (IV); and optionally
c2) isolating the compound of formula (IV) obtained.

21. A compound according to claim 1, wherein $R_1$ and $R_2$ are each independently methyl, ethyl or isopropyl group.

22. A compound according to claim 1, wherein $R_1$ and $R_2$ together form together -(CH$_2$)$_n$- in which n is 2 or 3.

23. A compound according to claim 8, wherein said compound is of Formula IA.

24. A compound according to claim 8, wherein said compound is of Formula IB.

25. A compound according to claim 1, wherein said compound is: E,Z- 1 -methoxy-2(2-(2-methyl-2-(1,3-dioxolan-2-yl)propoxy)-3-methoxy-phenyl)-ethene; or E,Z- 1 -methoxy-2(2-(2-methyl-2-(1     ,3-dioxolan-2-yl)propoxy)-4,5-dimethoxy-phenyl)-ethene.

26. A compound according to claim 1, wherein said compound is: E,Z-1-methoxy-2-(2-(2,2-dimethyl-3,3-diethoxy)propoxy-)-3-methoxy-phenyl)-ethene; E,Z-1-methoxy-2-(2-(2,2-dimethyl-3,3-diethoxy)propoxy-)-4,5-dimethoxy-phenyl)-ethene; or E,Z-1-methoxy-2-(2-(2,2-dimethyl-3,3-diethoxy)propoxy-)-5-methoxy-phenyl)-ethene.

* * * * *

UNITED STATES PATENT AND TRADEMARK OFFICE
CERTIFICATE OF CORRECTION

PATENT NO.        : 7,442,814 B2                                        Page 1 of 1
APPLICATION NO.   : 11/587488
DATED             : October 28, 2008
INVENTOR(S)       : Twana Saleh It is certified that error appears in the above-identified patent and that said Letters Patent is hereby corrected as shown below:

Column 22, lines 60-61, reads "$(C_1-C_{10})$aryl, and" should read -- $(C_1-C_{10})$aryl; and --
Column 23, line 17, reads "formula (I),and" should read -- formula (I), and --
Column 23, line 21, reads "reacting a base on" should read -- reacting a base with --
Column 24, line 16, reads "aldehyde formula" should read -- aldehyde of formula --
Column 24, lines 16-17, reads "formaldehyde (IX)" should read -- formaldehyde of formula (IX) --
Column 24, line 18, reads "hydroxyl compound" should read -- hydroxy compound --
Column 24, line 50, remove large space between "1" and ",3"

Signed and Sealed this

Twentieth Day of October, 2009

David J. Kappos
*Director of the United States Patent and Trademark Office*